United States Patent [19]

Picker

[11] Patent Number: 5,116,120
[45] Date of Patent: May 26, 1992

[54] GAS ANALYZER HAVING A TEST CHAMBER TRAVERSED BY RADIATION

[75] Inventor: Jürgen Picker, Wolfsburg, Fed. Rep. of Germany

[73] Assignee: Volkswagen AG, Fed. Rep. of Germany

[21] Appl. No.: 626,683

[22] Filed: Dec. 12, 1990

[30] Foreign Application Priority Data

Dec. 15, 1989 [DE] Fed. Rep. of Germany ....... 3941456

[51] Int. Cl.$^5$ ............................................. G01N 21/61
[52] U.S. Cl. .................................... 356/246; 356/440; 250/343
[58] Field of Search ............... 356/437, 439, 440, 413, 356/246, 236; 250/343, 576

[56] References Cited

U.S. PATENT DOCUMENTS

| | | | |
|---|---|---|---|
| 3,319,071 | 5/1967 | Werth et al. | 356/236 |
| 3,696,247 | 10/1972 | McIntosh et al. | 356/51 |
| 3,920,336 | 11/1975 | Sackett | 356/440 |
| 4,714,345 | 12/1987 | Schrader | 356/301 |
| 4,818,882 | 4/1989 | Nexo et al. | 250/343 |

FOREIGN PATENT DOCUMENTS 449287 12/1974 U.S.S.R. ............................... 356/246

OTHER PUBLICATIONS

Alan Bessen, "Pattern-recognition logic analyzes infrared signals", Industrial Electronics, Nov. 11, 1968, pp. 112–113.

*Primary Examiner*—Richard A. Rosenberger
*Attorney, Agent, or Firm*—Brumbaugh, Graves, Donohue & Raymond

[57] ABSTRACT

In the gas analyzer described in the specification, a test chamber housing for accommodating a volume of gas to be analyzed has a spherical shape and a spherical inner mirrored surface with windows to receive a radiation beam from a source and pass the beam to a detector. To provide different test distances through the chamber for the radiation beam, the source of radiation and the housing are movable relative to each other so that a reproducible change in the test distance can be achieved through multiple reflections on the inner mirrored surface of the housing.

3 Claims, 1 Drawing Sheet

GAS ANALYZER HAVING A TEST CHAMBER TRAVERSED BY RADIATION

BACKGROUND OF THE INVENTION

This invention relates to gas analyzers for determining constituents in a gas sample by detecting the energy loss of radiation transmitted through the gas sample.

Gas analyzers having a single chamber traversed by radiation absorbed by the gas are disclosed, for example, in U.S. Pat. No. 3,696,247, which describes such analysis of exhaust gases in motor vehicles, and in an article entitled "Pattern Recognition Logic Analyzes Infrared Signals" at page 112ff of the Nov. 11, 1968 issue of *Electronics*. In such gas analyzers, the radiation is repeatedly reflected by mirrors suitably disposed in the test chamber, so that it will reach the detector only after traversing a considerably greater distance through the gas than the direct distance between entrance and exit windows. As a result, the total distance traversed by the radiation through the gas may be greater than the maximum dimensions of the test chamber. This serves to increase the sensitivity of the gas analyzer without enlarging the chamber.

It is desirable to keep the chamber as small as possible since, after each measurement, the chamber must be flushed to remove gas residues and the smaller the gas volume and hence the chamber, the more quickly the flushing may be accomplished.

SUMMARY OF THE INVENTION

Accordingly, it is an object of the present invention to provide a new and improved gas analyzer which overcomes the disadvantages of the prior art.

Another object of the invention is to provide a gas analyzer having a reproducibly variable test distance, i.e., path length of radiation in the gas to be analyzed, with minimum cost and minimum size of the test chamber and therefore of the gas volume.

These and other objects of the invention are attained by providing a gas analyzer having a test chamber with a generally spherical reflective surface of constant curvature covering substantially the entire inner surface of the chamber, along with a test chamber support arrangement providing for reproducible variations in the relation between the test chamber and the radiation path.

In a preferred embodiment, the continuous curvature of the spherical test chamber mirror is utilized to render the test distance reproducibly variable by providing continuous relative adjustment between a radiation generator and the test chamber. With this arrangement, moreover, the gas volume is a minimum because of the spherical shape of the test chamber.

BRIEF DESCRIPTION OF THE DRAWINGS

Further objects and advantages of the invention will be apparent from a reading of the following description in conjunction with the accompanying drawings, in which.

DESCRIPTION OF PREFERRED EMBODIMENTS

Figure 1:
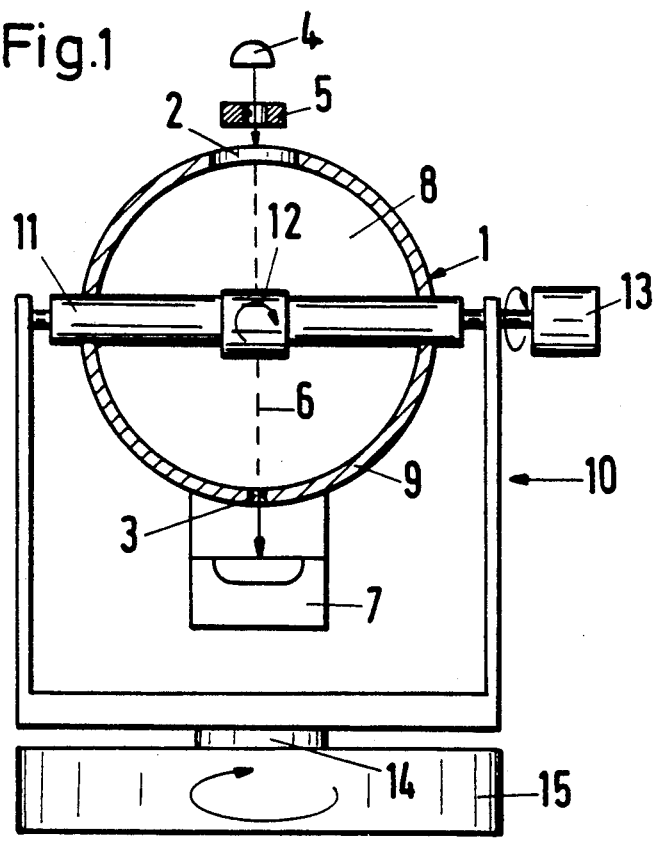
FIG. 1 is a schematic view, partly in section, showing the arrangement of a representative form of gas analyzer according to the invention which consists of a test chamber housing and support arrangement and a radiation detector along with a radiation generator disposed in a relative position to provide a minimum test distance.

In the typical embodiment of the invention shown in the drawings, a spherical test chamber housing 1 has an entrance window 2 and an exit window 3 for a beam of infrared radiation 6 received from a source 4 through an adjustable iris diaphragm 5. In the position of the housing 1 with respect to the source 4 shown in FIG. 1, the radiation passes directly through the windows 2 and 3 to a detector 7 which is mounted on the opposite side of the housing 1.

Electrical output signals produced by the radiation detector 7 are a measure of the intensity of the radiation beam 6 after traversing the volume of gas 8 in the test chamber housing 1. The intensity loss in the beam constitutes an indication of the content in the chamber of the particular gas to be analyzed. This analysis of the electrical signals from the detector 7 is performed in a computer (not shown) which receives signals from the detector and processes them in a conventional manner, which therefore need not be described here.

In the relative position of the housing 1, the diaphragm 5 and the detector 7 with respect to each other as shown in FIG. 1, the iris diaphragm 5 is adjusted to set the intensity of the radiation beam 6 to a reference value at which the detector 7 will produce a selected output signal. In this way it is possible, for example, to compensate for changes due to aging in the intensity of the radiation emitted by the source 4 before each measurement or before a group of measurements.

The arrangement shown in FIG. 1 provides the minimum test distance for the radiation beam 6. In many cases, the analyzer will fail to provide the required precision with the minimum test distance. Therefore, in accordance with the invention, a mirrored surface 9 is provided on the spherical inner surface of the housing 1 producing, in effect, an Ulbricht sphere, but with specular reflection.

Figure 2:
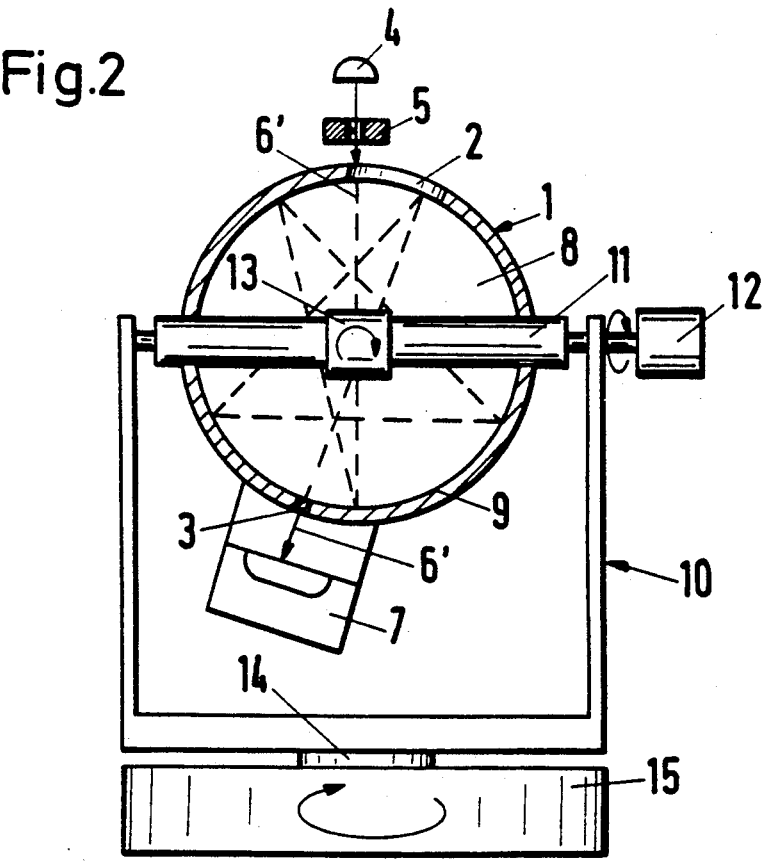
FIG. 2 is a schematic view similar to that of FIG. 1 showing the components in another relative position in which the test distance is considerably greater than the distance between radiation generator and detector.

FIG. 2 illustrates an arrangement in which the radiation source 4 and iris diaphragm 5 remain in the same spatial position shown in FIG. 1, but both the test chamber, represented by the spherical housing 1, and the detector 7 have changed their position relative to the radiation source 4 and the diaphragm arrangement 5. As a result, the mirrored inner surface 9 of the housing 1 intercepts the incident radiation beam 6' from the source since the exit window 3 is no longer opposite the source 4 and the diaphragm 5, the entrance window 2, however, being large enough to permit passage of the incident beam 6' into the test chamber. Thus, the beam 6' impinges on a reflecting area of the inner surface of the spherical housing 1. The orientation of the housing 1 is selected so that the reflected beam is not directed back into the region of the entrance window 2. Instead, it is incident on another area of the mirrored inner surface 9 of the housing, and is multiply reflected within the housing until it passes through the exit window 3 and arrives at the detector 7, which is large enough to receive radiation passing through the window 3 after reflection from regions of the surface 9 surrounding the window 2.

As will be apparent without further explanation, by such relative positioning of the housing 1 and the detector 7 with respect to the source 4 and diaphragm 5, the total test distance for the incident beam, i.e., the distance it traverses in the volume of gas 8 enclosed by the housing 1, can be reproducibly and continuously varied from the minimum test distance produced by the configuration shown in FIG. 1. For this purpose it is expedient to provide a housing support arrangement permitting relative motion in three coordinates, namely, two in the plane of the drawing and one perpendicular thereto. These adjusting means may be calibrated so that the operator can set specified test distances by means thereof. Because of the spherical inner shape of the test chamber housing 1, providing a mirrored surface 9 which is continuously curved, a large number of possible settings can be provided for a small gas volume 8 in the test chamber.

Considering now the adjusting means for the housing 1 in detail, the housing is supported by a cardanic suspension 10, having a bearing ring 11 which can be moved by means of three step motors 12, 13 and 14, with respect to a baseplate 15. The motors thus provide motion of the housing 1 and the detector 7 about three mutually perpendicular axes relative to the radiation generator 4. This motion is indicated by arrows at the output shafts of the step motors. The same result can, of course, be obtained by interchanging the locations of the radiation source 4 and the detector 7 or by mounting the housing 1 in fixed position and supporting the radiation source 4 in a correspondingly movable manner.

If desired, the step motors may be energized in accordance with a preassigned program.

The invention thus provides a gas analyzer having a chamber with an especially small gas volume without thereby limiting the possibilities of measurement.

Although the invention has been described herein with reference to specific embodiments, many modifications and variations therein will readily occur to those skilled in the art. Accordingly, all such variations and modifications are included within the intended scope of the invention.

I claim:

1. A gas analyzer comprising a radiation source, a radiation detector, a test chamber of spherical configuration to receive gas to be analyzed including an inner housing surface of spherical configuration and having entrance and exit windows for receiving radiation emitted by the radiation source and passing radiation to the detector, respectively, a mirror surface of constant curvature extending over substantially the entire inner housing surface wherein the radiation attenuation in the gas measured by the detector may be used to characterize the gas in the test chamber, and support means for providing positioning adjustment between the test chamber and one of the source and the detector in order to vary the test distance.

2. A gas analyzer according to claim 1, wherein the mirror surface is the inner housing surface.

3. A gas analyzer according to claim 1 or claim 2, wherein the support means comprises a cardanic suspension having a plurality of step motors for providing relative motion between the test chamber and one of the source and the detector.

* * * * *